(12) United States Patent
Suyama et al.

(10) Patent No.: US 8,600,005 B2
(45) Date of Patent: *Dec. 3, 2013

(54) RADIATION DETECTION DEVICE, RADIATION IMAGE ACQUIRING SYSTEM, AND METHOD FOR DETECTING RADIATION

(75) Inventors: Toshiyasu Suyama, Hamamatsu (JP); Tadashi Maruno, Hamamatsu (JP); Toshihide Sasaki, Hamamatsu (JP); Junichi Sonoda, Hamamatsu (JP); Shinji Takihi, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/600,516

(22) Filed: Aug. 31, 2012

(65) Prior Publication Data
US 2013/0044862 A1      Feb. 21, 2013

Related U.S. Application Data

(63) Continuation of application No. 12/615,675, filed on Nov. 10, 2009, now Pat. No. 8,280,005.

(30) Foreign Application Priority Data

Nov. 11, 2008   (JP) ................ P2008-288924

(51) Int. Cl.
*H05G 1/64* (2006.01)
*G01N 23/087* (2006.01)

(52) U.S. Cl.
USPC ............ 378/98.8; 378/53; 378/57; 378/98.9; 378/98.11; 250/370.09

(58) Field of Classification Search
USPC ....................... 378/53, 57, 98.8, 98.9, 98.11; 250/370.09
See application file for complete search history.

(56) References Cited

U.S. PATENT DOCUMENTS

| 4,445,226 A | 4/1984 | Brody |
|---|---|---|
| 5,481,584 A | 1/1996 | Tang et al. |

(Continued)

FOREIGN PATENT DOCUMENTS

| JP | 6-027249 | 2/1994 |
|---|---|---|
| JP | 7-306165 | 11/1995 |

(Continued)

*Primary Examiner* — Allen C. Ho
(74) *Attorney, Agent, or Firm* — Drinker Biddle & Reath LLP

(57) ABSTRACT

An X-ray image acquiring system capable of improving the detection accuracy of a foreign substance contained in a subject is provided. An X-ray image acquiring system irradiates X-rays to a subject having a predetermined thickness from an X-ray source, and detects X-rays transmitted through the subject in a plurality of energy ranges. The X-ray image acquiring system includes a low-energy detector for detecting, in a low-energy range, X-rays having been transmitted through a region R1 extending in a thickness direction within the subject, a high-energy detector for detecting, in a high-energy range, X-rays having been transmitted through a region R2 extending in a thickness direction within the subject, and a timing control section for controlling detection timing of X-rays in the low-energy detector and the high-energy detector so that an inspecting region located at a predetermined site within the subject is included in the region R1 and the region R2.

15 Claims, 18 Drawing Sheets

(56) References Cited

U.S. PATENT DOCUMENTS

| | | | |
|---|---|---|---|
| 5,570,403 | A | 10/1996 | Yamazaki et al. |
| 5,841,832 | A | 11/1998 | Mazess et al. |
| 6,188,747 | B1 | 2/2001 | Geus et al. |
| 6,198,795 | B1 | 3/2001 | Naumann et al. |
| 6,370,223 | B1 | 4/2002 | Gleason et al. |
| 6,600,805 | B2 | 7/2003 | Hansen |
| 7,724,869 | B2 | 5/2010 | Wang et al. |
| 8,223,922 | B2 * | 7/2012 | Suyama et al. ............ 378/98.9 |
| 8,280,005 | B2 * | 10/2012 | Suyama et al. ............ 378/98.9 |
| 2002/0168046 | A1 | 11/2002 | Hansen |
| 2010/0119038 | A1 | 5/2010 | Suyama et al. |

FOREIGN PATENT DOCUMENTS

| | | |
|---|---|---|
| JP | 8-068768 | 3/1996 |
| JP | 10-318943 | 12/1998 |
| JP | 11-316198 | 11/1999 |
| JP | 2001-099790 | 4/2001 |
| JP | 2002-168803 | 6/2002 |
| JP | 2003-279503 | 10/2003 |

* cited by examiner

Fig.5
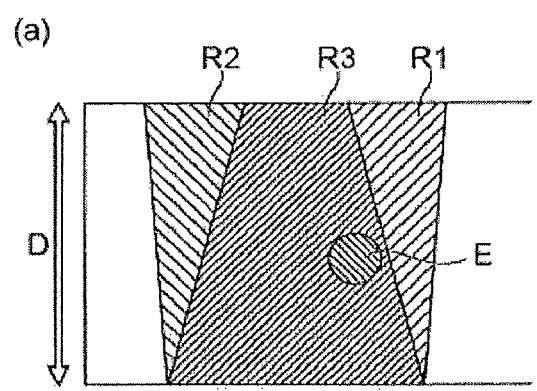
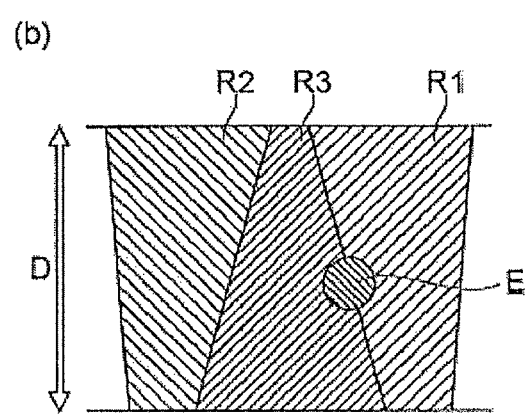

Fig.7
(a)
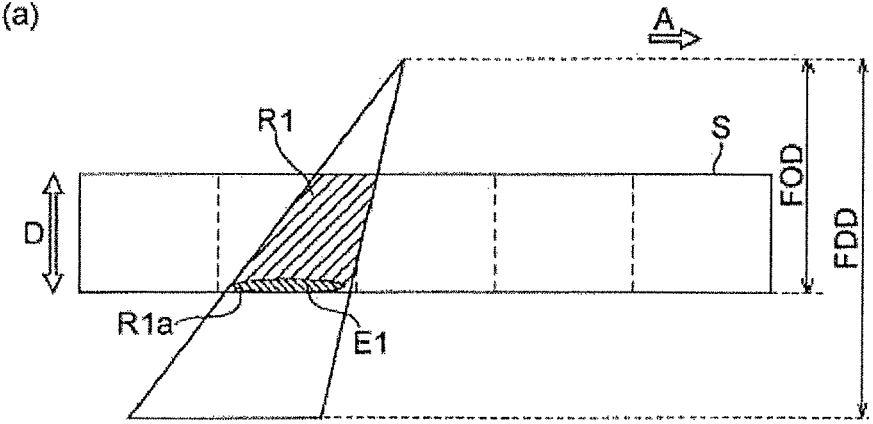
(b)
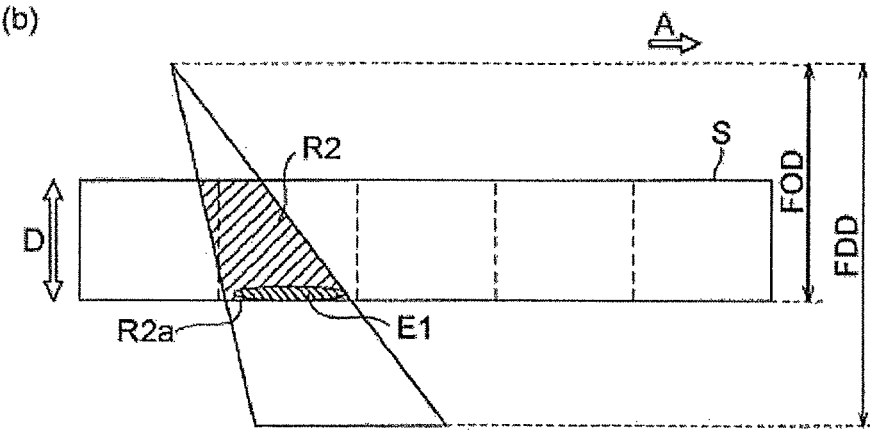
(c)
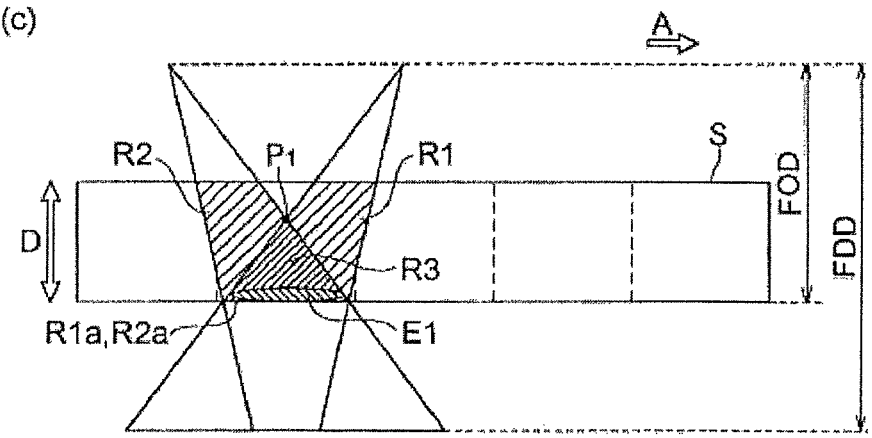

Fig.9
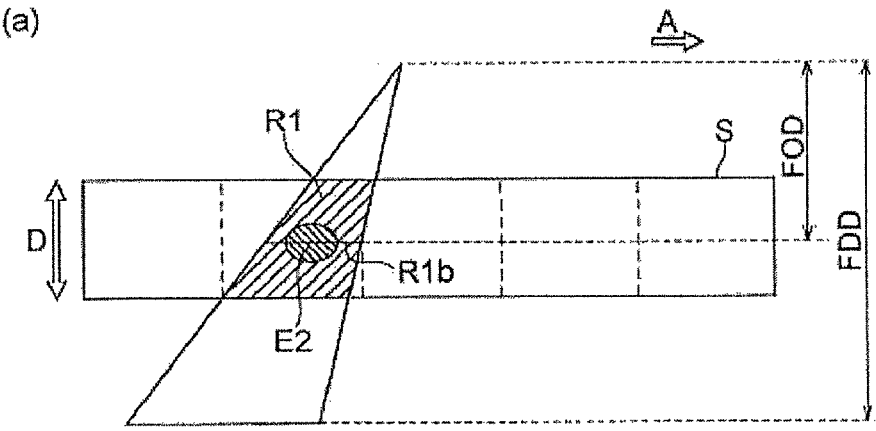
(a)
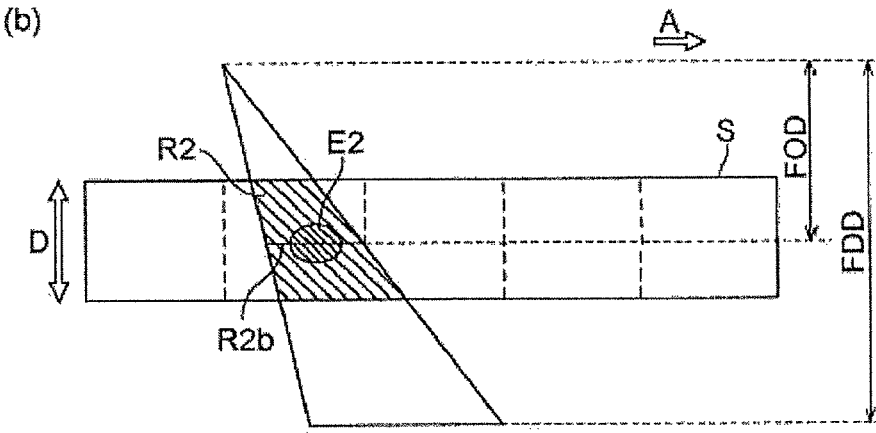
(b)
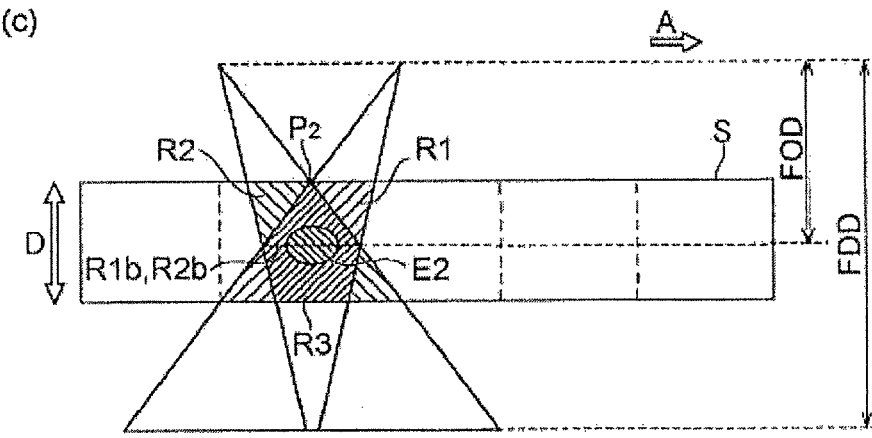
(c)

Fig.11
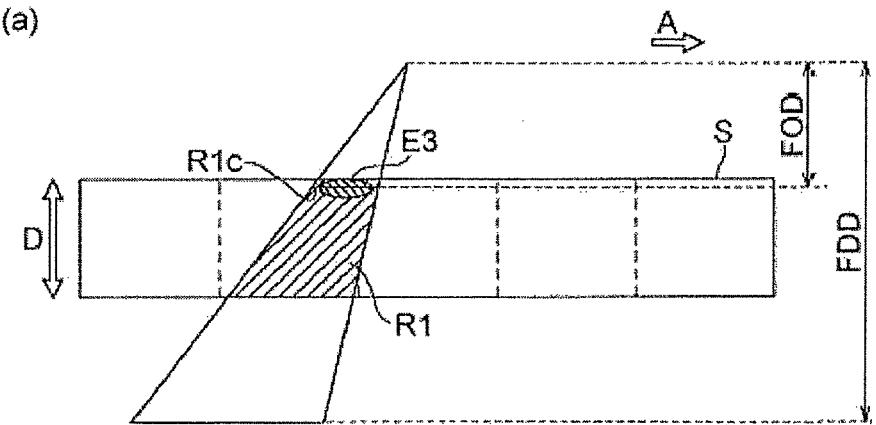
(a)
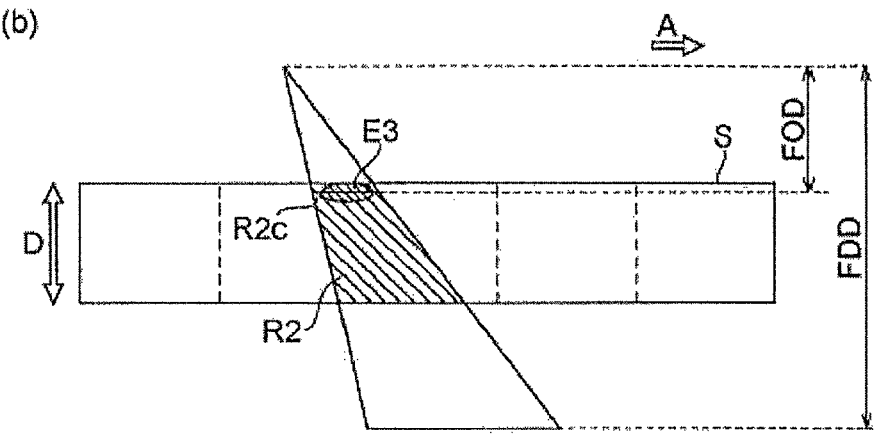
(b)
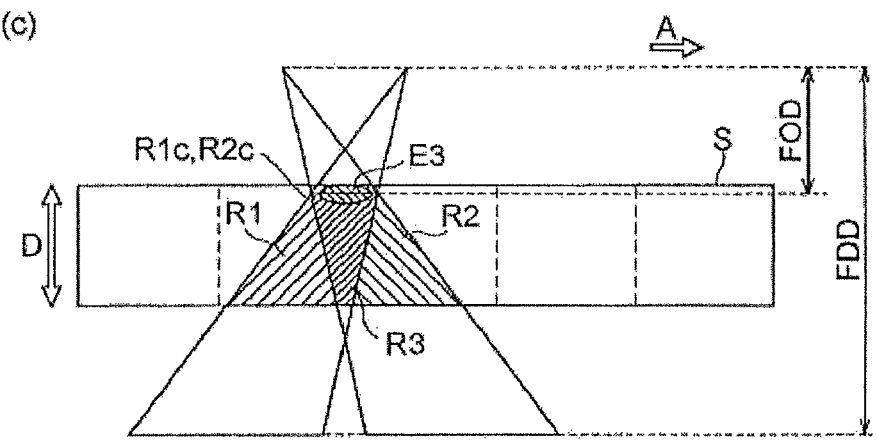
(c)

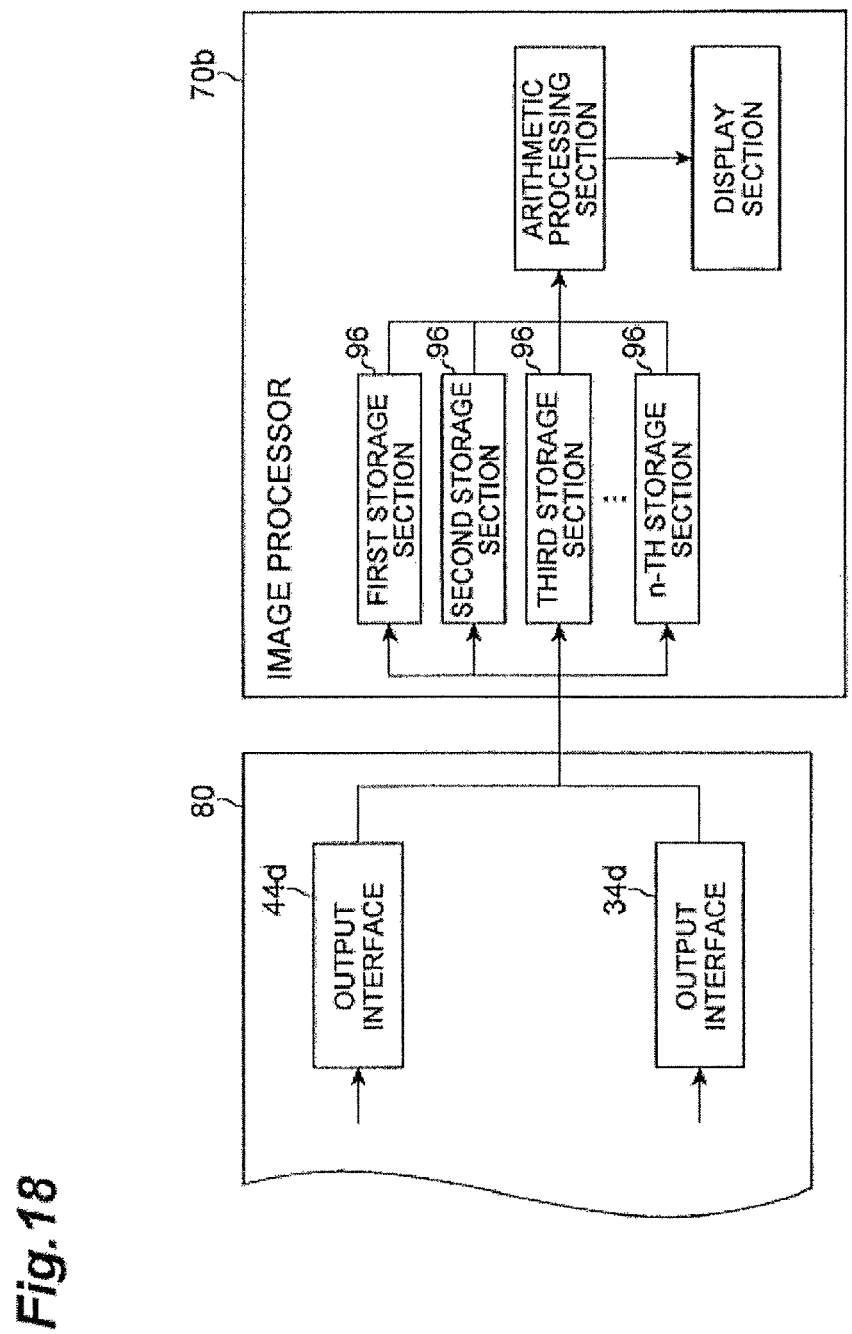

RADIATION DETECTION DEVICE, RADIATION IMAGE ACQUIRING SYSTEM, AND METHOD FOR DETECTING RADIATION

This is a continuation application of copending prior application Ser. No. 12/615,675, filed on Nov. 10, 2009 now U.S. Pat. No. 8,280,005, which is incorporated by reference herein in its entirety.

BACKGROUND OF THE INVENTION

1. Field of the Invention

The present invention relates to a radiation detection device, a radiation image acquiring system, and a method for detecting radiation.

2. Related Background Art

Conventionally, it has been common to allow X-rays to transmit through a subject being a specimen such as food or drugs and make an inspection based on a transmission X-ray image thereof to determine the existence of a foreign substance in a subject. For such an inspection, an X-ray detection device including an X-ray source for irradiating X-rays to the subject and a linear line sensor for detecting a transmission image of X-rays irradiated to the subject from the X-ray source has been used.

However, in the case of detection by a single line sensor with no energy discrimination function, because of the absence of an energy discrimination function, the detection accuracy may decline due to a difference in the composition of a foreign substance contained in the subject (for example, a difference of whether being bone or meat or whether being cartilage or a foreign substance in a meat inspection) and a difference in thickness. Therefore, it has been proposed to arrange in parallel two line sensors for detecting X-rays of different energy ranges, acquire a subtraction image being a difference data image from X-ray images detected by these two line sensors, and thereby improve the detection accuracy irrespective of the composition and thickness of a foreign substance contained in a subject (refer to, for example, Japanese Published Unexamined Patent Application H10-318943).

SUMMARY OF THE INVENTION

However, according to investigation by the inventors of the present invention, it has been found that an image part indicating a foreign substance etc., may have unclear edges in a subtraction image in an attempt to acquire a subtraction image from X-ray data of a subject detected by two line sensors arranged in parallel. For this reason, detection of a foreign substance etc., contained in a subject cannot always be performed with accuracy by merely using two line sensors.

The present invention has therefore been made in view of such problems, and an object thereof is to provide a radiation detection device, a radiation image acquiring system, and a method for detecting radiation capable of improving the detection accuracy of a foreign substance etc., contained in a subject.

The inventors have devoted themselves to continuous study in order to attain the above-mentioned object, and directed their attention to the fact that, when detecting transmitted radiation through a subject by a radiation detection device including two line sensors to thereby inspect whether a foreign substance exists, a site where a foreign substance etc., can be contained is sometimes limited to a predetermined region in a thickness direction of the subject in some cases. Then, it has been discovered that not by such an improvement in clearness of a subtraction image of the entire subject as commonly assumed, but by an improvement in clearness of a subtraction image in at least the above-mentioned predetermined region (hereinafter, referred to as an "inspecting region") of the subject, the detection accuracy of a foreign substance etc., included in the subject can be improved even if a subtraction image of the entire subject is not clear. Then, the inventors completed the present invention upon obtaining the knowledge that the detection accuracy in a foreign substance inspection by two line sensors can be improved by performing adjustment of detection timing so that the inspecting region is reliably included in a transmission X-ray region detected by both two line sensors.

More specifically, a radiation detection device according to the present invention, which is a radiation detection device that irradiates radiation to a subject having a predetermined thickness from a radiation source, and detects radiation transmitted through the subject in a plurality of energy ranges, includes: a first detector for detecting, in a first energy range, radiation having been transmitted through a first region extending in a thickness direction within the subject; a second detector for detecting, in a second energy range, radiation having been transmitted through a second region extending in a thickness direction within the subject; and a timing control section for controlling detection timing of radiation in the first detector and the second detector so that an inspecting region located at a predetermined site within the subject is included in the first region and the second region.

Moreover, a method for detecting radiation of the present invention, which is a method for detecting radiation in a radiation detection device including a radiation source for irradiating radiation to a subject, a first detector for detecting radiation in a first energy range, a second detector for detecting radiation in a second energy range, and a timing control section for controlling detection timing of radiation in the first detector and the second detector, includes: an irradiation step of the radiation source irradiating radiation to the subject having a predetermined thickness; a first detection step of the first detector detecting, in a first energy range, radiation irradiated in the irradiation step and transmitted through a first region extending in a thickness direction within the subject; a second detection step of the second detector detecting, in a second energy range, radiation irradiated in the irradiation step and transmitted through a second region extending in a thickness direction within the subject; and a timing control step of a timing control section controlling detection timing of radiation in the first detector and the second detector so that an inspecting region located at a predetermined site within the subject is included in the first region and the second region.

In the radiation detection device and the method for detecting radiation, the timing control section controls detection timing of radiation in the first detector and the second detector so that the inspecting region located at the predetermined site within the subject is included in the first region and the second region. This makes the subject having a predetermined thickness include the inspecting region in both the first region through which radiation to be detected by the first detector has been transmitted and the second region through which radiation to be detected by the second detector has been transmitted. Therefore, the inspecting region is reliably detected by radiation data detected by each detector. As a result, an unclear edge part is reduced in, of a subtraction image of the subject, at least a part corresponding to the inspecting region, so that the detection accuracy of a foreign substance etc., contained in the subject can be improved.

Moreover, a radiation image acquiring system according to the present invention preferably includes: the radiation detection device mentioned above; and a timing calculating section for calculating detection timing of radiation in the first detector and the second detector. Provision of the timing calculating section simplifies the calculation of detection timing. As such a timing calculating section, it is preferable to, for example, calculate detection timing based on the thickness-direction position of a predetermined site within the subject where the inspecting region is located. Moreover, as another timing calculating section, it is preferable to, in the first region, calculate a first reference plane intersecting with a thickness direction of the subject based on a thickness-direction position where the inspecting region is located as well as, in the second region, calculate a second reference plane being at the same thickness-direction position as that of the first reference plane and intersecting with the thickness direction, and calculate the detection timing so that the first reference plane and the second reference plane are overlapped with each other. Thus, the calculation using a thickness-direction position and reference planes based on the inspecting region allows calculating a timing where the inspecting region is reliably included in both the first region and the second region.

Moreover, it may be possible that the first detector and the second detector detect radiation having been transmitted through an adjusting subject having a test piece placed at a site thereof corresponding to the inspecting region, and the timing calculating section, based on radiation data having been transmitted through the adjusting subject detected by the first detector and the second detector, calculates detection timing of the radiation in the first detector and the second detector so that the test piece is included in the first region and the second region. Using such an adjusting member allows simply calculating detection timing in the first detector and the second detector.

Moreover, it may be possible to include a composite image generating section for generating a composite image by synthesizing radiation data detected by the first detector with radiation data detected by the second detector, and that the composite image generating section generates a composite image targeting a plurality of inspecting regions different in thickness-direction position from one set of radiation data detected by the first detector in one first region and a plurality of sets of radiation data detected by the second detector in a plurality of second regions. This allows inspecting the inspecting regions located at various thickness-direction positions all at once.

BRIEF DESCRIPTION OF THE DRAWINGS

FIG. 5(a) is a view showing a state where an inspecting region E is included in an X-ray irradiating region, and FIG. 5(b) is a view showing a state where an inspecting region E is not included in an X-ray irradiating region.

FIG. 7 are views showing an example of calculating a delay time T when the inspecting region E is located in the vicinity of a bottom surface of the subject S.

FIG. 9 are views showing an example of calculating a delay time T when the inspecting region E is located in the vicinity of a lower middle portion of the subject S.

FIG. 11 are views showing an example of calculating a delay time T when the inspecting region E is located in the vicinity of an upper middle portion of the subject S.

FIG. 18 is a diagram showing another example of a device configuration including a storage section for retaining X-ray data detected by a detector.

DESCRIPTION OF THE PREFERRED EMBODIMENTS

Figure 1:
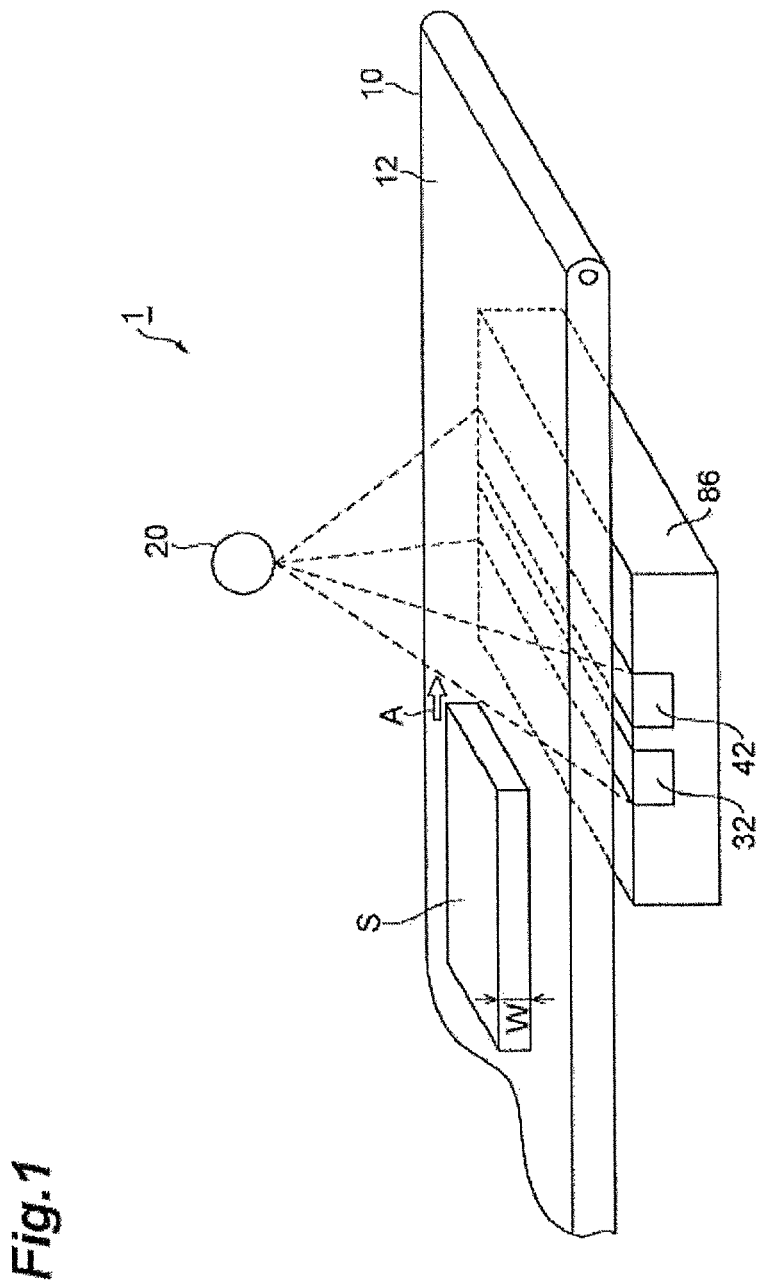
FIG. 1 is a perspective view of an X-ray image acquiring system according to the present embodiment.

Hereinafter, a preferred embodiment of an X-ray image acquiring system according to the present invention will be described with reference to the drawings. Also, the same or corresponding parts are denoted with the same reference numerals in description of the drawings, and overlapping description will be omitted.

Figure 2:
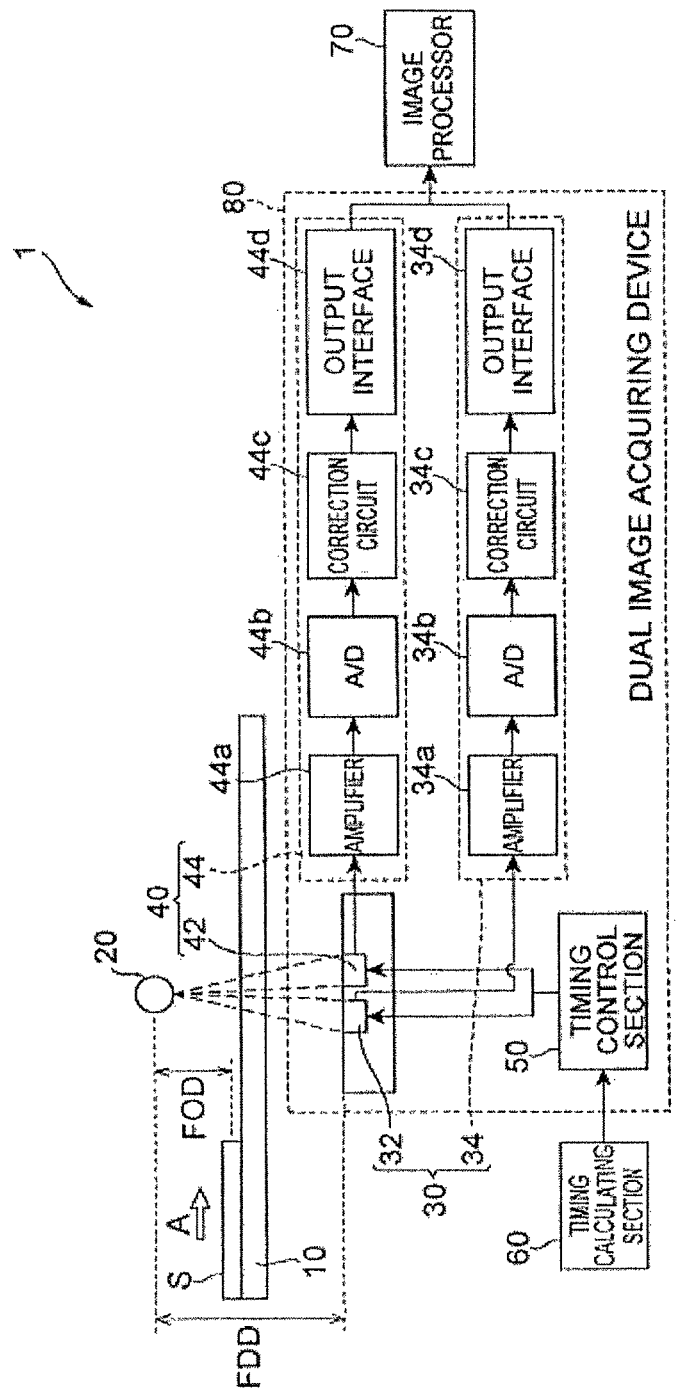
FIG. 2 is a schematic configuration diagram of the X-ray image acquiring system according to the present embodiment.

FIG. 1 is a perspective view of an X-ray image acquiring system according to the present embodiment, and FIG. 2 is a schematic configuration diagram of the X-ray image acquiring system according to the present embodiment. As shown in FIG. 1 and FIG. 2, the X-ray image acquiring system (radiation image acquiring system) 1 is an apparatus that irradiates X-rays (radiation) from an X-ray source (radiation source) to a subject S having a predetermined thickness (for example, a fixed thickness W), and detects, of the irradiated X-rays, transmitted X-rays having been transmitted through the subject S in a plurality of energy ranges. The X-ray image acquiring system 1 is used for detecting, by using a transmission X-ray image, a foreign substance (a foreign substance settled in a liquid, or floating on the surface, one layer of a liquid separated in layers, a specific height of not only a liquid but also a solid, gas, etc., for example, when the height of inspection changes depending on the shape of the subject) and voids contained in a specific site (hereinafter, referred to as an "inspecting region E") of the subject S, or carrying out, if the subject S is prepared by bonding or laminating a different substance at the inspecting region E, observation of a bonding surface thereof (for example, observation of incorporation of a foreign substance or voids in the vicinity of a bonding surface, and a specific layer of an electronic substrate) etc.

The X-ray image acquiring system 1 includes a belt conveyor 10, an X-ray irradiator 20, a low-energy image acquiring section 30, a high-energy image acquiring section 40, a timing control section 50, a timing calculating section 60, and an image processor (a composite image generating section) 70. The low-energy image acquiring section 30, the high-energy image acquiring section 40, and the timing control section 50 compose a dual image acquiring device (radiation detection device) 80.

The belt conveyor 10, as shown in FIG. 1, includes a belt portion 12 on which the subject S is placed. The belt conveyor 10 makes the belt portion 12 move in a conveying direction A (from an upstream side at the left-hand side of FIG. 1 to a downstream side at the right-hand side of FIG. 1) to thereby convey the subject S in the conveying direction A at a predetermined conveying speed M. The conveying speed M of the subject S is, for example, 48 m/minute. The belt conveyor 10 can, if necessary, be changed in speed by a belt conveyor control section (not shown) to a conveying speed of, for example, 24 m/minute or 96 m/minute. Here, examples of the subject S to be conveyed by the belt conveyor 10 include food such as edible meat and electronic components, each of which has a predetermined thickness W.

Figure 4:
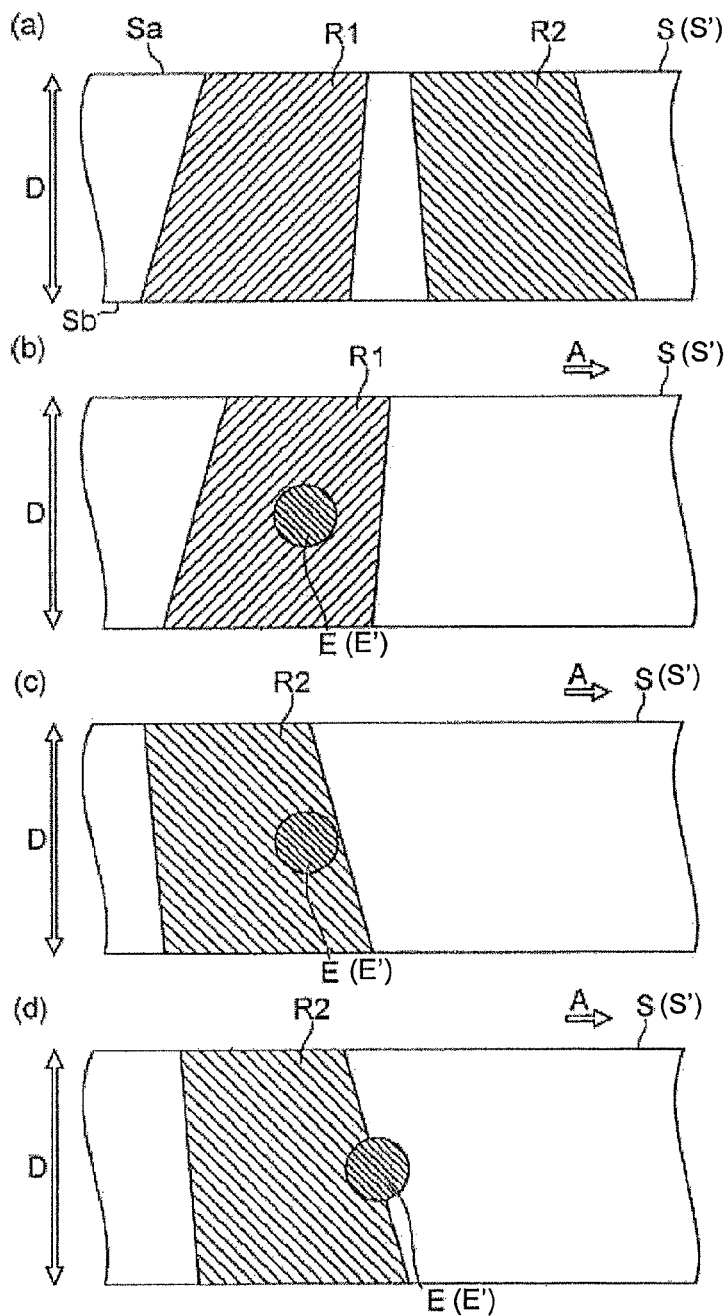
FIG. 4 are views each showing an X-ray irradiating region in a subject S.

The X-ray irradiator 20 is a device that irradiates X-rays to the subject S as an X-ray source. The X-ray irradiator 20 is a point source, which irradiates while diffusing X-rays at a predetermined angular range in a fixed irradiation direction. The X-ray irradiator 20 is arranged above the belt portion 12 at a predetermined distance from the belt portion 12 so that the direction of X-ray irradiation is oriented to the belt portion 12 and the diffusing X-rays extend in the entire width direction (direction perpendicular to the conveying direction A) of the subject S. The X-ray irradiator 20, in a length direction (direction parallel to the conveying direction A) of the subject S, has a predetermined divided range in the length direction as its irradiation range. Referring to, for example, FIG. 4(a) showing an X-ray irradiation range of the subject S, X-rays irradiated from the X-ray irradiator 20 are transmitted through a region R1, R2. The region R1, R2 is a three-dimensional region extending in a thickness direction D within the subject S, and is shaped so as to broaden from an upper surface Sa (the side close to the X-ray irradiator 20 being a point source) toward a lower surface Sb (the side close to the belt conveyor 10). In addition, the X-ray irradiator 20 is structured so that X-rays are irradiated to the subject S across the length direction thereof as a result of the subject S being conveyed by the belt conveyor 10 in the conveying direction A.

The low-energy image acquiring section 30 includes a low-energy detector (first detector) 32 and a low-energy image correcting section 34.

The low-energy detector 32 detects, of the X-rays irradiated from the X-ray irradiator 20, X-rays having been transmitted through a predetermined region (first region) R1 of the subject S in a low-energy range (first energy range) to generate low-energy image data. The low-energy detector 32 is formed of, for example, a linear line sensor with a length equal to or more than the width of the subject S, and arranged below an upstream side of the belt portion 12 so as to be perpendicular to the conveying direction A with an X-ray detection plane thereof opposed to the X-ray irradiator 20.

The low-energy image correcting section 34 is a part that amplifies and corrects the low-energy image data generated by the low-energy detector 32. The low-energy image correcting section 34 includes an amplifier 34a that amplifies low-energy image data, an A/D converter 34b that A/D-converts the low-energy image data amplified by the amplifier 34a, a correction circuit 34c that carries out a predetermined correction processing for the low-energy image data converted by the A/D converter 34b, and an output interface 34d that externally outputs the image data corrected by the correction circuit 34c.

The high-energy image acquiring section 40 includes a high-energy detector (second detector) 42 and a high-energy image correcting section 44.

The high-energy detector 42 detects, of the X-rays irradiated from the X-ray irradiator 20, X-rays having been transmitted through a predetermined region (second region) R2 of the subject S in a high-energy range (second energy range) to generate high-energy image data. The high-energy detector 42 is formed of, for example, a linear line sensor with a length equal to or more than the width of the subject S, and arranged below a downstream side of the belt portion 12 so as to be perpendicular to the conveying direction A with an X-ray detection plane thereof opposed to the X-ray detector 20.

The high-energy image correcting section 44 is a part that amplifies and corrects the high-energy image data generated by the high-energy detector 42. The high-energy image correcting section 44 includes an amplifier 44a that amplifies high-energy image data, an A/D converter 44b that A/D-converts the high-energy image data amplified by the amplifier 44a, a correction circuit 44c that carries out a predetermined correction processing for the high-energy image data converted by the A/D converter 44b, and an output interface 44d that externally outputs the image data corrected by the correction circuit 44c.

Figure 3:
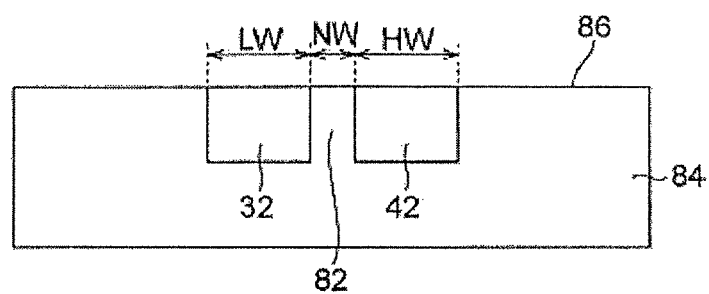
FIG. 3 is a side view of a dual energy sensor according to the present embodiment.

Here, the low-energy detector 32 and the high-energy detector 42 will be described in detail. As shown in FIG. 3, the low-energy detector 32 is a line sensor with a sensing width of LW along the conveying direction A. In addition, the high-energy detector 42 is a line sensor with a sensing width of HW along the conveying direction A. The sensing width of LW and the sensing width of HW, in the present embodiment, are the same width, and for example, 0.8 mm. Moreover, the low-energy detector 32 and high-energy detector 42 thus configured are arranged and fixed onto a base 84 in parallel with a dead zone region 82 having a dead zone width NW (for example, 0.4 mm) sandwiched therebetween along the convening direction A, and compose a dual energy sensor 86, which is a semiconductor detector.

Figure 6:
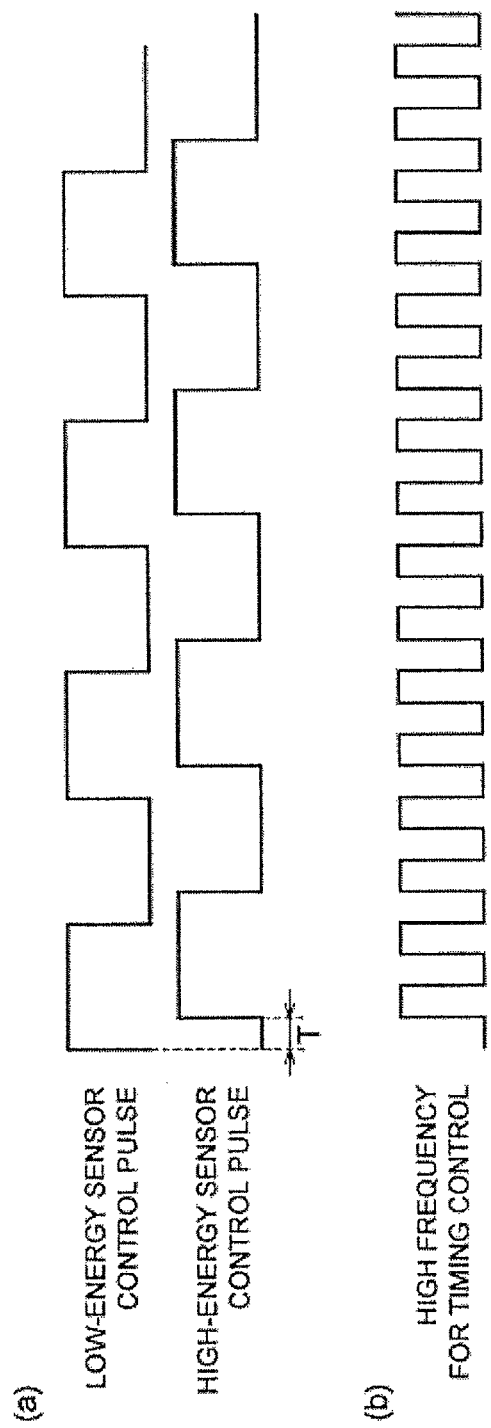
FIG. 6(a) is a diagram showing a control pulse signal of each detector in the X-ray image acquiring system according to the present embodiment.
FIG. 6(b) is a diagram showing a high-frequency signal for generating a control pulse signal.

The low-energy detector 32 having the sensing width LW, based on control pulses (refer to FIG. 6(a)) having a predetermined cycle, detects X-rays having been transmitted through one region R1 in the subject S by the detecting surface with the sensing width LW. Then low-energy sensor 32 repeats this to, as schematically shown in, for example, FIG. 4(b), detect transmitted X-rays corresponding to the region R1 at each detection timing. Moreover, the high-energy detector 42 having the sensing width HW also, as with the low-energy detector 32, as schematically shown in, for example, FIG. 4(c), detects transmitted X-rays corresponding to the region R2 at each detection timing.

In addition, as the low-energy detector 32 and the high-energy detector 42 to compose the dual energy sensor 86, for example, one with an energy discrimination function for which a low-energy cutting filter is arranged on a high-energy sensor may be used. Alternatively, a scintillator for converting X-rays in a low-energy range to visible light and a scintillator for converting X-rays in a high-energy range to visible light may be used to provide both detectors 32, 42 with different wavelength sensitivities, so as to allow detecting different energy ranges. In addition, filters may be arranged on scintilators having different wavelength sensitivities. Further, there may be one with an energy discrimination function by a direct conversion method of CdTe (cadmium telluride) or the like.

The timing control section 50 controls the detection timing of transmitted X-rays in the low-energy detector 32 and the detection timing of transmitted X-rays in the high-energy detector 42 so that the inspecting region E located at a predetermined part of the subject S is included in the region R1, R2. The timing control section 50, to the low-energy detector 32, outputs low-energy sensor control pulses of a predetermined frequency as shown in FIG. 6(a) etc. Moreover, the timing control section 50, to the high-energy detector 42, outputs a high-energy sensor control pulse signal of the same frequency as that of low-energy sensor control pulses and delayed in the rising spot of pulses by a predetermined time T (hereinafter, sometimes referred to as a "delay time").

The timing control section 50, by changing the delay time T, performs control so that the inspecting region E located at a predetermined site of the subject S is included in both of the region R1 for detection by the low-energy detector 32 and the region R2 for detection by the high-energy detector 42, as shown in FIGS. 4(b) and (c). Then, when control has been performed by the timing control section 50 so that the inspecting region E is included in the region R1, R2, the inspecting region E comes to be included in a shared region R3 between the region R1 and the region R2, as shown in FIG. 5(a). This indicates that information (such as whether a foreign substance exists) in the inspecting region E has been reliably included in both X-ray transmission image data detected and generated by each detector 32, 42, and in such a case, a clear energy subtraction image can be obtained without mismatch between both images to be detected by both detectors 32, 42. In addition, when control has not been performed by the timing control section 50 so that the inspecting region E is included in the region R1, R2, X-ray detection is performed at a detection timing as in, for example, FIG. 4(d), so that as shown in FIG. 5(b), the inspecting region E is not entirely included in the shared region R3 between the region R1 and the region R2.

When the timing control section 50 generates the control pulse signal including the delay time T, a PLL (Phase Locked Loop) or the like is used to generate a high-frequency signal for timing control shown in FIG. 6(b). As such a high-frequency signal, for example, in the case of driving at a pixel clock required for sensor drive of about 200 kHz in the energy detector 32, 42 or the like, using a signal of a frequency of 20 MHz or more about 100 times that frequency allows meticulous control. In the case of a pixel clock for sensor drive of about 1 MHz, using likewise a signal of 100 MHz or more allows meticulous control. The higher the frequency of a high-frequency signal, the more flexibly a change in conveying speed M, pixel clock, or the like can be responded to, and thus meticulous control can be performed. In addition, a high-frequency oscillator for a delay signal may be used, in place of the PLL, to generate a delay control pulse signal.

The timing calculating section 60 calculates a delay time T, which is a detection timing to be used by the timing control section 50. The timing calculating section 60 calculates the delay time T by the following formula (I) based on the dead zone width NW of the dead zone region 82 in the dual energy sensor 86, speed at which the subject S passes through the dead zone region 82 (that is, the conveying speed M), and a magnification ratio R of X-rays to be transmitted through the subject S.

$$T = NW/(R \times M) \quad (1)$$

Here, the magnification ratio R means a ratio (FDD/FOD) of FOD (Focus Object Distance, refer to FIG. 2) being a distance between the X-ray irradiator 20 and an inspection center of the subject S and FDD (Focus Detector Distance, refer to FIG. 2) being a distance between the X-ray irradiator 20 and each detector 32, 42. For example, in FIG. 2, when FOD is 1 and FDD is 2, the magnification ratio R is 2.

The timing calculating section 60, based on the formula (1), calculates a delay time T in the detection timing by the high-energy detector 42 with respect to the detection timing by the low-energy detector 32. In the present embodiment, the inspection center of the subject S in FOD for calculating the magnification ratio R is provided as a thickness-direction position within the subject S where the inspecting region E is located. That is, when, for example, the vicinity of a surface part of the subject S is provided as the inspecting region E, the distance between an upper surface of the subject S and the X-ray irradiator 20 equals FOD. Alternatively, when the vicinity of a middle of the subject S is provided as the inspecting region E, the distance between a middle in a thickness direction D of the subject S and the X-ray irradiator 20 equals FOD. Still alternatively, when the vicinity of a bottom of the subject S is provided as the inspecting region E, the distance between a lower bottom surface of the subject S and the X-ray irradiator 20 equals FOD. Then, the timing calculating section 60 outputs the calculated delay time T to the timing control section 50 as detection timing. In addition, the dead zone width NW, the conveying speed M, and the magnification ratio R are input to the timing calculating section 60 via an input section or the like.

The image processor 70 is a device that performs an arithmetic processing for obtaining difference data between the low-energy image data detected and generated by the low-energy detector 32 and the high-energy image data detected and generated by the high-energy detector 42, and generates an energy subtraction image, which is a composite image. Both energy image data to be input to the image processor 70 have been controlled in terms of detection timing, by the timing control section 50, so that the inspecting region E of the subject S is included in each other's image data, and thus the image processor 70 generates an energy subtraction image that is clear in, at least, a part corresponding to the inspecting region E by a predetermined arithmetic processing. Then, the image processor 70 outputs to display the generated energy subtraction image on a display or the like. This output display allows visually confirming a foreign substance contained in the subject S. In addition, without outputting to display an energy subtraction image, a foreign substance contained in the subject S may be detected directly from image data by a detection processing in the image data.

Here, a calculation example of the delay time T in detection timing to be used by the timing control section 50 will be described by using FIG. 7 to FIG. 12. A subject S to be used for the description is supposed to have a length of 4.0 mm in a direction along the conveying direction A, have a thickness in the thickness direction D equal to ⅓ the distance (FDD) between the X-ray irradiator 20 and each detector 32, 42, and supposed to be one where the length of the inspecting region E along the conveying direction A is smaller than the sensing width LW, HW of each detector 32, 42. It is supposed that the sensing width LW, HW of each detector 32, 42 is 0.8 mm, the dead zone width NW of the dead zone region 82 is 0.4 mm, and the conveying speed of the belt conveyor 10 is 0.8 mm/millisecond (48 m/minute).

Figure 8:
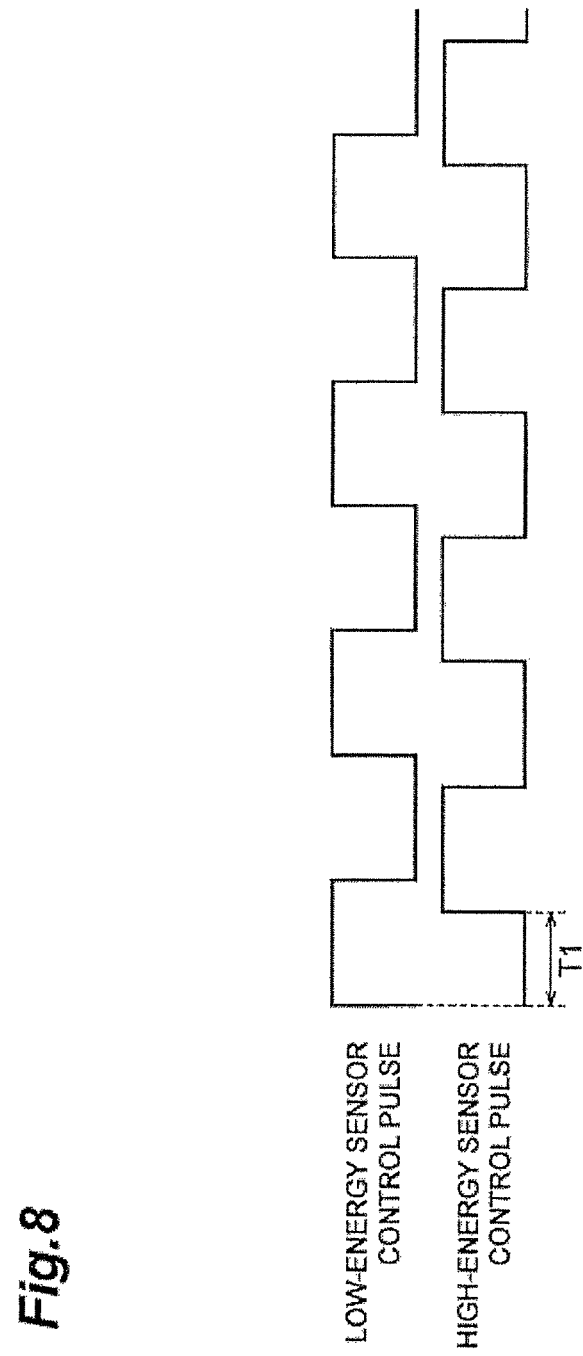
FIG. 8 is a diagram showing a control pulse signal of each detector in the calculation example of FIG. 7.

First, description will be given of a case where the inspecting region E is located in the vicinity of a lower bottom surface of the subject S (an inspecting region E1), by using FIG. 7 and FIG. 8. In this case, because, as shown in FIG. 7, the inspecting region E1 is located in the vicinity of the lower bottom surface of the subject S, the inspection center of the subject S is provided as FOD indicating the bottom surface of the subject S and FDD are set as FOD:FDD=2:3. When a magnification ratio R is determined from the set value, the magnification ratio R is 1.5. When the timing calculating section 60 then determines a delay time T1 by counting in the various conditions and magnification ratio R described above for (formula 1), the delay time T1 is, for example, 0.333 milliseconds. The timing calculating section 60 outputs the calculated delay time T1 to the timing control section 50.

The timing control section 50, when having been input with the delay time T1 from the timing calculating section 60, generates a control pulse signal (refer to FIG. 8) of each detector 32, 42 including the delay time T1, and outputs the control pulse signal to each detector 32, 42. Due to the output of the control pulse signal, the low-energy detector 32 detects X-rays having been transmitted through the region R1 shown in FIG. 7(a) at a predetermined timing, while the high-energy detector 42 detects X-rays having been transmitted through the region R2 shown in FIG. 7(b) at a predetermined timing including the delay time T1. Then, as schematically shown in FIG. 7(c), in the image processor 70, image data for which the inspecting region E1 is included in a shared region R3 formed by the region R1 and the region R2 intersected at an intersection P1 is used to generate an energy subtraction image.

In addition, timing control by the delay time T1 through calculation of the above formula (I) can be paraphrased as being the following control. More specifically, the timing calculating section 60 calculates, in the region R1, a first reference plane R1a that intersects with the thickness direction D of the subject based on a thickness-direction position (bottom surface position) where the inspecting region E1 is located. Next, the timing calculating section 60 calculates, in the second region R2, a second reference plane R2a that is at the same thickness-direction position as that of the first reference plane R1a (that is, the bottom surface position) and intersects with the thickness direction D of the subject S. Then, the timing calculating section 60 calculates a detection timing where the first reference plane R1a in the region R1 and a second reference plane R2a in the region R2 are mostly overlapped or coincident with each other, and the timing control section 50 controls each detector 32, 42 based on such detection timing. Also by such control, image data for which the inspecting region E1 is included in the shared region R3 can be used to generate an energy subtraction image.

Figure 10:
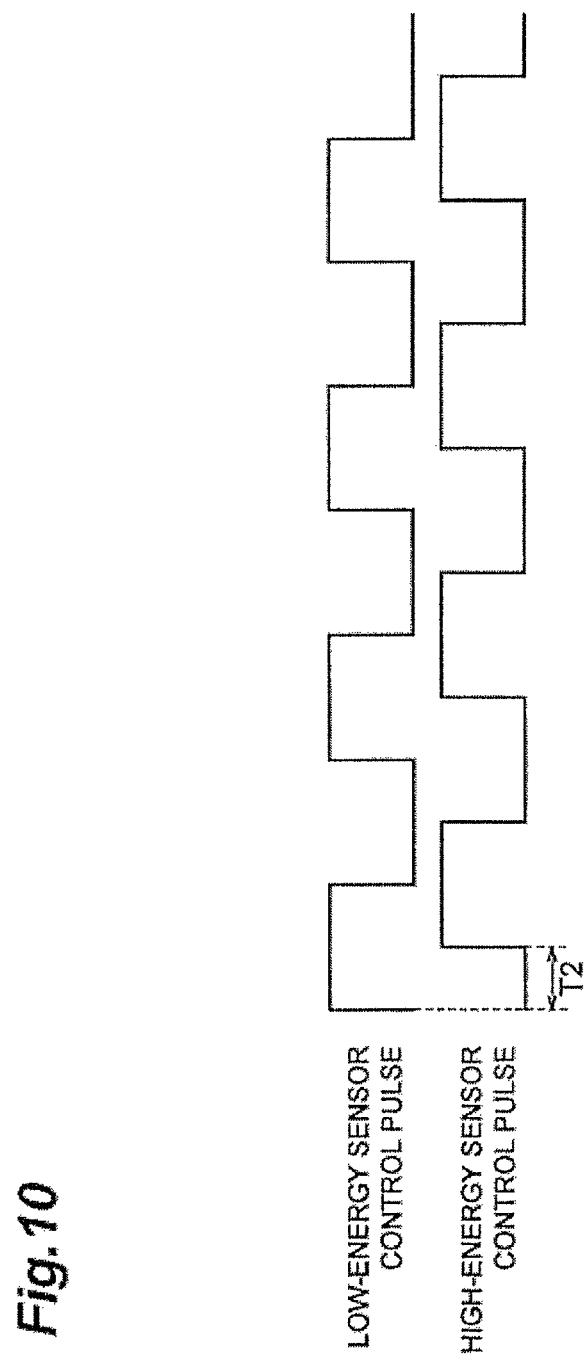
FIG. 10 is a diagram showing a control pulse signal of each detector in the calculation example of FIG. 9.

Next, description will be given of a case where the inspecting region E is located in a middle portion of the subject S (an inspecting region E2), by using FIG. 9 and FIG. 10. In this case, because, as shown in FIG. 9, the inspecting region E2 is located in the vicinity of the middle portion of the subject S, the inspection center of the subject S is provided as FOD indicating the vicinity of the middle portion of the subject S and FDD are set as, for example, FOD:FDD=1:2. When a magnification ratio R is determined from the set value, the magnification ratio R is 2. When the timing calculating section 60 then determines a delay time T2 by counting in the various conditions and magnification ratio R described above for (formula 1), the delay time T2 is, for example, 0.25 milliseconds. The timing calculating section 60 outputs the calculated delay time T2 to the timing control section 50.

The timing control section 50, when having been input with the delay time T2 from the timing calculating section 60, generates a control pulse signal (refer to FIG. 10) of each detector 32, 42 including the delay time T2, and outputs the control pulse signal to each detector 32, 42. Due to the output of the control pulse signal, the low-energy detector 32 detects X-rays having been transmitted through the region R1 shown in FIG. 9(a) at a predetermined timing, while the high-energy detector 42 detects X-rays having been transmitted through the region R2 shown in FIG. 9(b) at a predetermined timing including the delay time T2. Then, as schematically shown in FIG. 9(c), in the image processor 70, image data for which the inspecting region E2 is included in a shared region R3 formed by the region R1 and the region R2 intersected at an intersection P2 is used to generate an energy subtraction image.

In addition, timing control by the delay time T2 through calculation of the above formula (I) can be paraphrased as being the control using reference planes described above. That is, the timing calculating section 60 calculates a detection timing where a first reference plane R1b in the region R1 and the second reference plane R2b in the region R2 are mostly overlapped or coincident with each other, as shown in FIGS. 9(a) and (b), and when the timing control section 50 controls each detector 32, 42 based on such detection timing, image data for which the inspecting region E2 is included in the shared region R3 can be used to generate an energy subtraction image.

Figure 12:
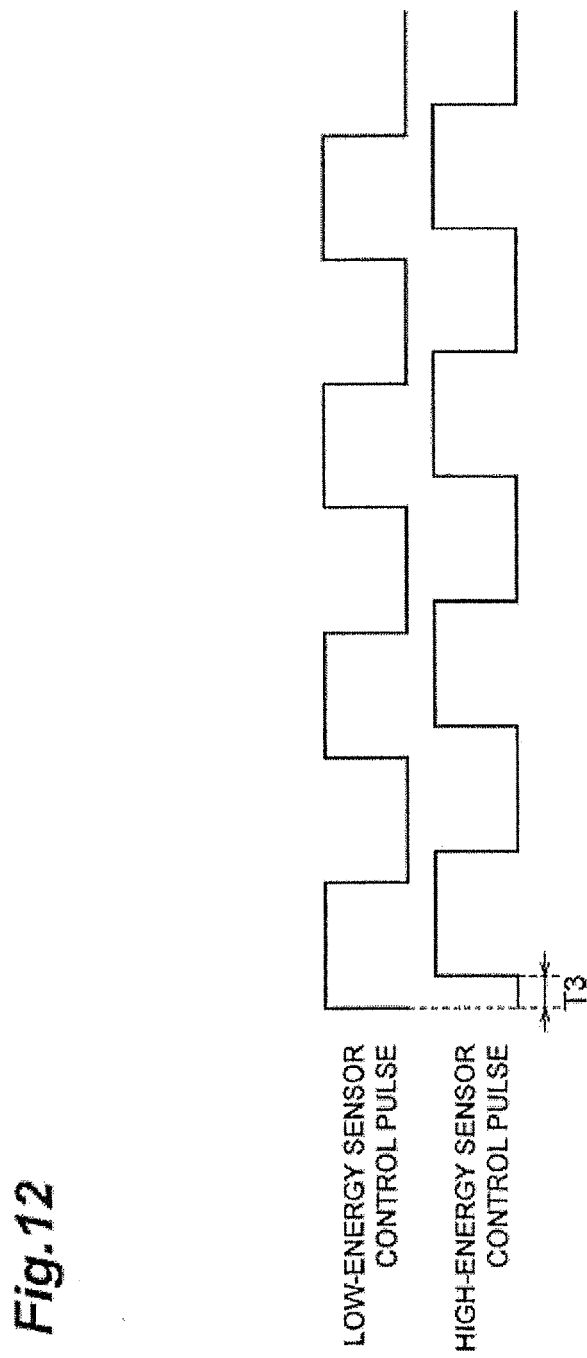
FIG. 12 is a diagram showing a control pulse signal of each detector in the calculation example of FIG. 11.

Then, description will be given of a case where the inspecting region E is located at an upper side of the subject S (an inspecting region E3), by using FIG. 11 and FIG. 12. In this case, because, as shown in FIG. 11, the inspecting region E3 is located in the vicinity of the upper side of the subject S, the inspection center of the subject S is provided as FOD indicating the vicinity of the upper side of the subject S and FDD are set as, for example, FOD:FDD=1:3. When a magnification ratio R is determined from the set value, the magnification ratio R is 3. When the timing calculating section 60 then determines a delay time T3 by counting in the various conditions and magnification ratio R described above for (formula 1), the delay time T3 is, for example, 0.167 milliseconds. The timing calculating section 60 outputs the calculated delay time T3 to the timing control section 50.

The timing control section 50, when having been input with the delay time T3 from the timing calculating section 60, generates a control pulse signal (refer to FIG. 12) of each detector 32, 42 including the delay time T3, and outputs the control pulse signal to each detector 32, 42. Due to the output of the control pulse signal, the low-energy detector 32 detects X-rays having been transmitted through the region R1 shown in FIG. 11(a) at a predetermined timing, while the high-energy detector 42 detects X-rays having been transmitted through the region R2 shown in FIG. 11(b) at a predetermined timing including the delay time T3. Then, as schematically shown in FIG. 11(c), in the image processor 70, image data for which the inspecting region E3 is included in a shared region R3 formed by the region R1 and the region R2 intersected is used to generate an energy subtraction image.

In addition, timing control by the delay time T3 through calculation of the above formula (I) can be paraphrased as being the control using reference planes described above. That is, the timing calculating section 60 calculates a detection timing where a first reference plane R1c in the region R1 and the second reference plane R2c in the region R2 are mostly overlapped or coincident with each other, as shown in FIGS. 11(a) and (b), and when the timing control section 50 controls each detector 32, 42 based on such detection timing, image data for which the inspecting region E3 is included in the shared region R3 can be used to generate an energy subtraction image.

When calculating the delay time T in detection timing as in the above, there is indeed a method for calculation by inputting the position (position in the thickness direction D and position in the length direction) of the inspecting region E via an input section, but a method for calculation by using an adjusting subject S' arranged at the same site thereof corresponding to the inspecting region E as in the subject S with a test piece E' that can be detected by X-rays may be adopted. At this time, as the adjusting subject S', one that is the same in shape and material as the subject S may be used. Alternatively, one that is the same in shape as and different in material from the subject S may be used so that information required for performing timing control can be obtained, or a jig for timing control may be used. More specifically, such an adjusting subject S' is actually placed on the belt conveyor 10 and conveyed, and the low-energy detector 32 and the high-energy detector 42 detect radiation having been transmitted through the adjusting subject S'. Then, the timing calculating section 60, based on the amount of mismatch etc., in the X-ray data (including an energy subtraction image) having been transmitted through the adjusting subject S' detected by the low-energy detector 32 and the high-energy detector 42, may calculate or adjust detection timing of X-rays in the low-energy detector 32 and the high-energy detector 42 so that the test piece E' is included in the region R1 and the region R2. Using such an adjusting subject S' allows the timing calculating section 60 to simply calculate detection timing in the low-energy detector 32 and the high-energy detector 42.

As has been described above, in the X-ray detection device 1, the timing control section 50 controls detection timing of X-rays in the low-energy detector 32 and the high-energy detector 42 so that the inspecting region E located at the predetermined site within the subject S is included in the region R1 and the region R2. This makes the subject S having a predetermined thickness W include the inspecting region E in both the region R1 through which X-rays to be detected by the low-energy detector 32 have been transmitted and the region R2 through which X-rays to be detected by the high-energy detector 42 have been transmitted. Therefore, the inspecting region E is reliably detected by X-ray data detected by each detector 32, 42. As a result, an unclear edge part is reduced in, of a subtraction image of the subject S, at least a part corresponding to the inspecting region E, so that the detection accuracy of a foreign substance etc., contained in the subject S can be improved.

Moreover, in the above-mentioned embodiment, provided is the timing calculating section 60 for calculating X-ray detection timing in the low-energy detector 32 and the high-energy detector 42. Provision of the timing calculating section 60 simplifies the calculation of detection timing. Such a timing calculating section 60 is structured so as to, for example, calculate FOD etc., based on the thickness-direction position of a predetermined site within the subject S where the inspecting region E is located to determine the geometric magnification R based on FOD etc., and calculate detection timing based on the thus obtained magnification R, the conveying speed M, the dead zone width NW, etc. Moreover, in a different perspective, the timing calculating section 60 calculates, in the region R1, the first reference plane R1$a$, R1$b$, R1$c$ intersecting with the thickness-direction of the subject S based on the thickness-direction position where the inspecting region E is located as well as calculates, in the region R2, the second reference plane R2$a$, R2$b$, R2$c$ being at the same thickness-direction position as that of the first reference plane R1$a$, R1$b$, R1$c$ and intersecting with the thickness direction of the subject S, and calculates a detection timing so that the first reference plane R1$a$, R1$b$, R1$c$ and the second reference plane R2$a$, R2$b$, R2$c$ are overlapped or coincident with each other. Thus, the calculation using a thickness-direction position and reference planes based on the inspecting region E allows calculating a timing where the inspecting region E is reliably included in both the region R1 and the region R2.

Moreover, the low-energy detector 32 and the high-energy detector 42 may be structured so as to detect X-rays having been transmitted through the adjusting subject S' arranged at a site thereof corresponding to the inspecting region E with a test piece E', and the timing calculating section 60 may be structured so as to, based on X-ray data having been transmitted through the adjusting subject S' detected in the low-energy detector 32 and the high-energy detector 42, detect X-ray detection timing in the low-energy detector 32 and the high-energy detector 42 so that the test piece E' is included in the region R1 and the region R2. Using such an adjusting subject S' allows simply calculating detection timing in the low-energy detector 32 and the high-energy detector 42. The detection timing may be set by an operator after observing mismatch in an image of the adjusting subject S', or may be set by calculating the amount of mismatch by a program in a PC or image processor that has imported image data. Alternatively, it may be possible to implement a circuit or program for calculating the amount of mismatch inside a detector of the dual image acquiring device 80 or the like and set the detection timing based on the amount of mismatch inside the detector.

Figure 13:
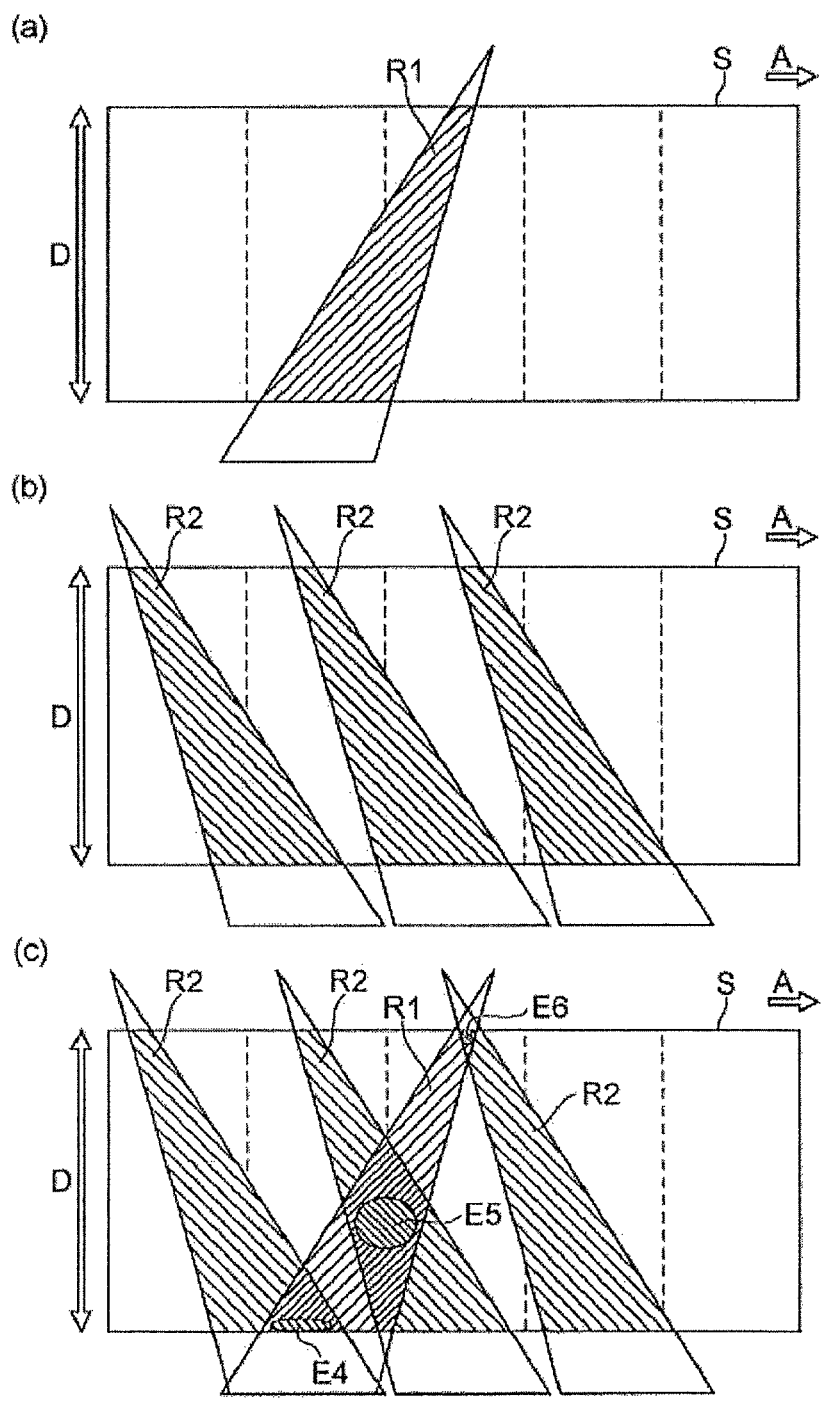
FIG. 13 are views showing a state where a plurality of inspecting regions E different in thickness-direction position are inspected by use of X-ray data transmitted through a plurality of irradiating regions.
Figure 14:
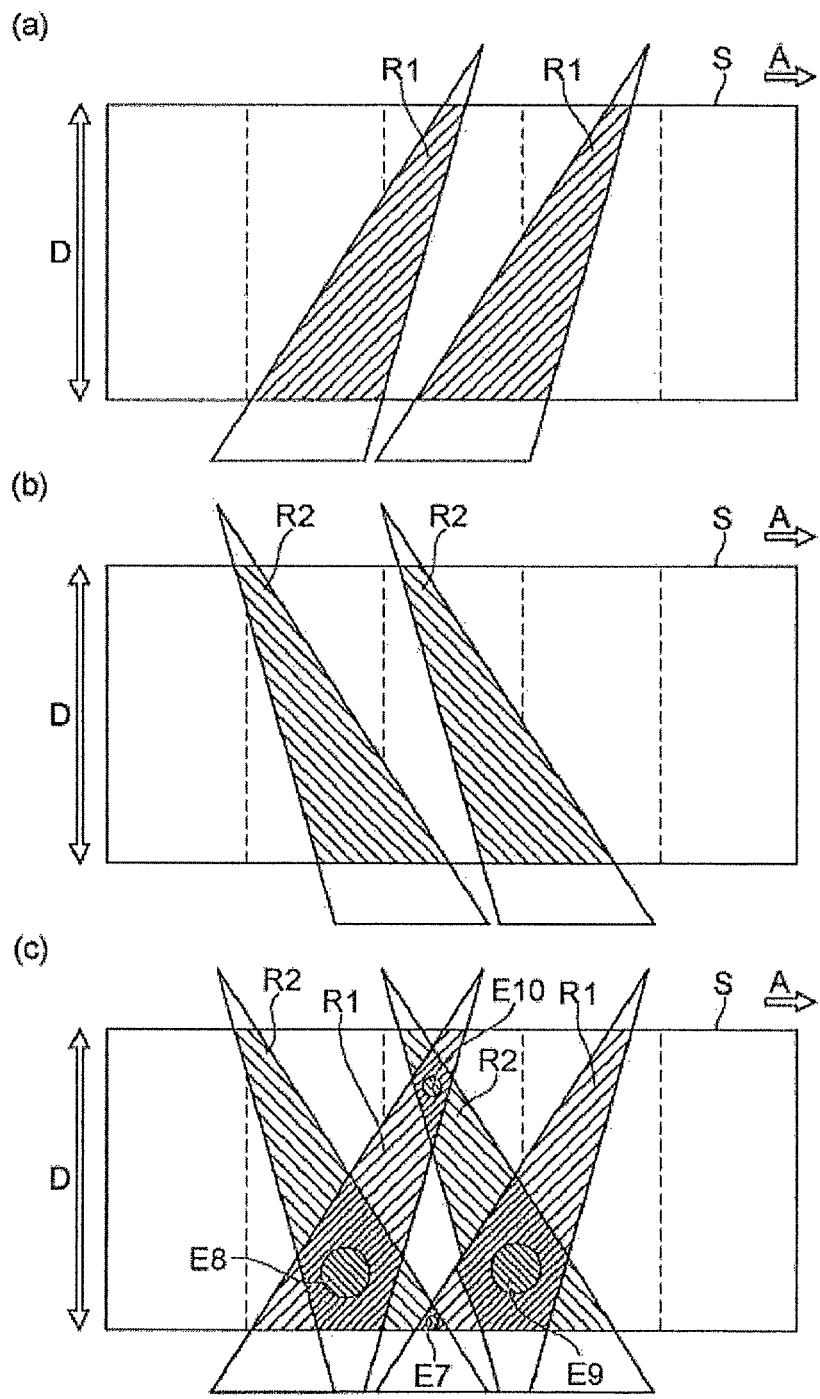
FIG. 14 are views showing another state where a plurality of inspecting regions E different in thickness-direction position are inspected by use of X-ray data transmitted through a plurality of irradiating regions.

Although a preferred embodiment of the present invention has been described in the above, the present invention is by no means limited to the above-mentioned embodiment, and various modifications can be made. For example, in the above-mentioned embodiment, transmitted X-ray data having been transmitted through one region R1 in a low-energy range and transmitted X-ray data having been transmitted through one region R2 in a high-energy range are used to generate an energy subtraction image of the subject S including the inspecting region E for inspection of a foreign substance etc., in the inspecting region E, however, as shown in FIG. 13, transmitted X-ray data having been transmitted through one region R1 in a low-energy range (refer to FIG. 13($a$)) and transmitted X-ray data having been transmitted through three regions R2 in a high-energy range (refer to FIG. 13($b$)) may be used for inspection of a foreign substance etc., in inspecting regions E4, E5, and E6 different in thickness-direction position (refer to FIG. 13($c$)). Alternatively, as shown in FIG. 14, transmitted X-ray data having been transmitted through two regions R1 in a low-energy range (refer to FIG. 14($a$)) and transmitted X-ray data having been transmitted through two regions R2 in a high-energy range (refer to FIG. 14($b$)) may be used for inspection of a foreign substance etc., in inspecting regions E7, E8, E9, and E10 different in thickness-direction position (refer to FIG. 14($c$)). Such a foreign substance inspection in different thickness-direction positions is used when, for example, a foreign substance inspection of cans different in height size is performed.

Figure 15:
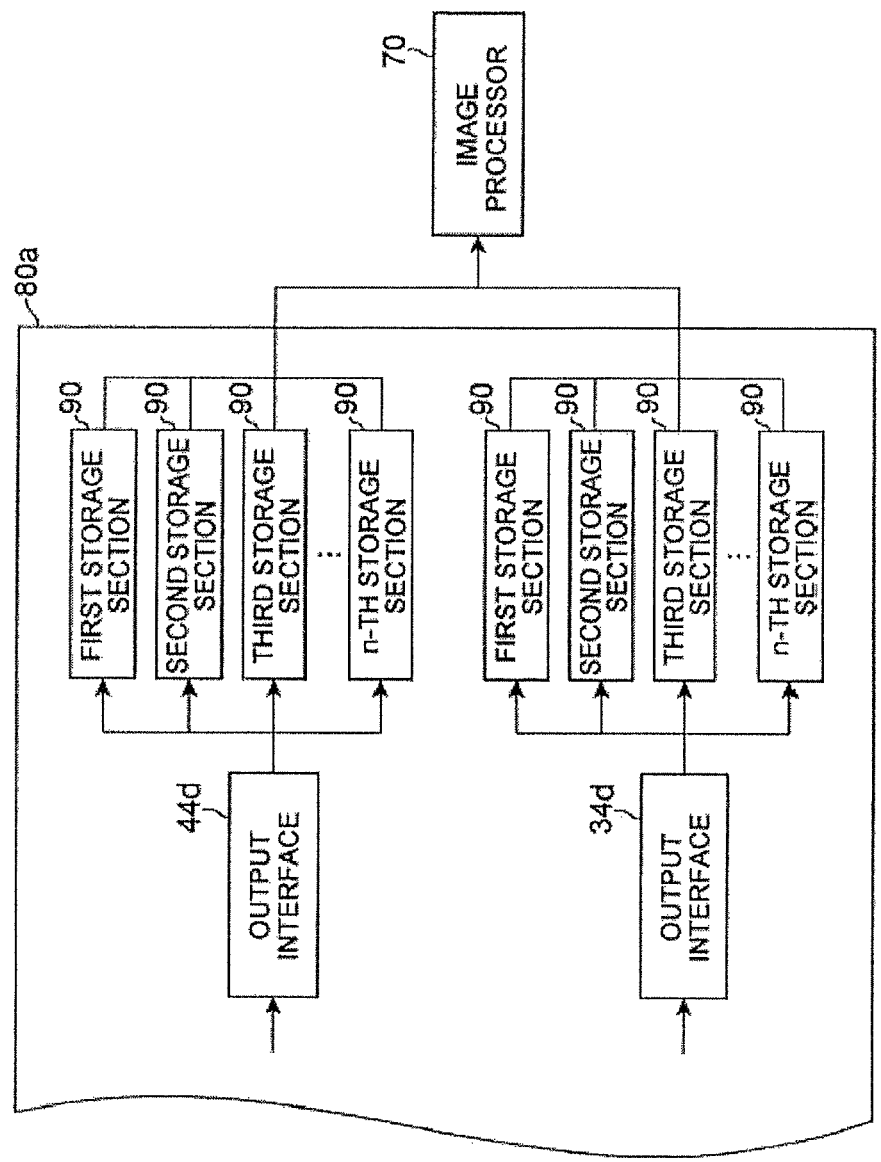
FIG. 15 is a diagram showing an example of a device configuration including a storage section for retaining X-ray data detected by a detector.
Figure 16:
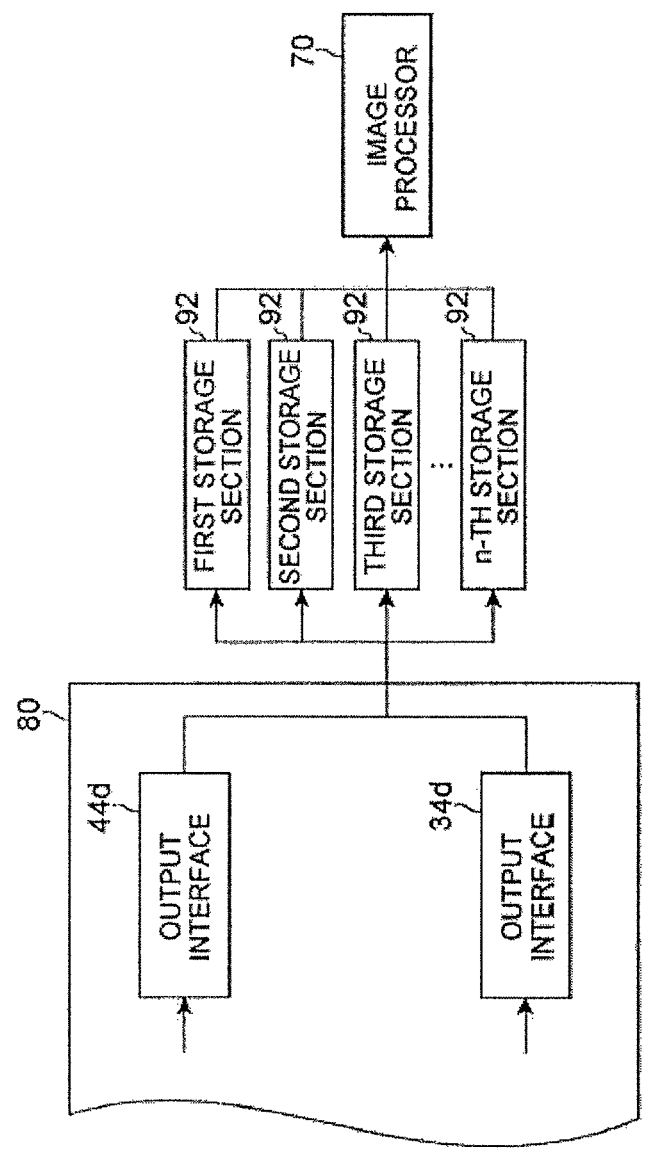
FIG. 16 is a diagram showing another example of a device configuration including a storage section for retaining X-ray data detected by a detector.
Figure 17:
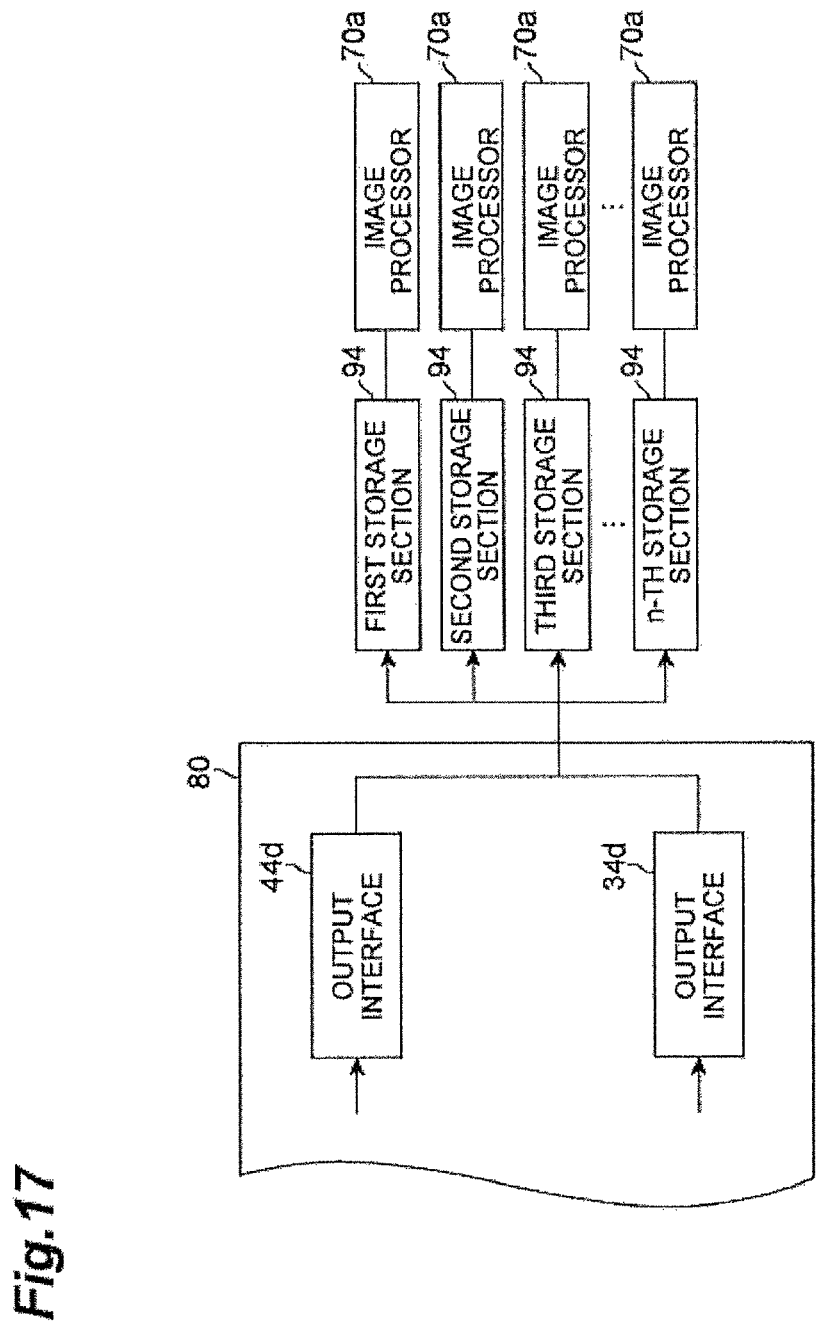
FIG. 17 is a diagram showing another example of a device configuration including a storage section for retaining X-ray data detected by a detector.

When a plurality of sets of transmitted X-ray data are used for inspection of a foreign substance etc., in an inspecting region, there exist methods that use memories as means for performing data comparison. For example, as one of the methods, by preparing a memory inside each detector 32, 42, holding therein either transmitted X-ray data at low energy or transmitted X-ray data at high energy, and using the data stored in the memory for comparison, a foreign substance inspection and the like in inspecting regions at different thickness-direction positions can be performed. Alternatively, as shown in FIG. 15, by preparing, in a dual image acquiring device 80a, a storage section 90 for holding both transmitted X-ray data at low energy and transmitted X-ray data at high energy, and using the data stored in the storage section 90 for comparison, a foreign substance inspection and the like in inspecting regions at different thickness-direction positions can be performed. Alternatively, as shown in FIG. 16, by preparing, between the dual image acquiring device 80 and the image processor 70, a storage section 92 for holding both transmitted X-ray data at low energy and transmitted X-ray data at high energy, and using the data stored in the storage section 92 for comparison, a foreign substance inspection and the like in inspecting regions at different thickness-direction positions can be performed. Alternatively, as shown in FIG. 17, by preparing, between the dual image acquiring device 80 and a plurality of image processors 70a, a storage section 94 for holding both transmitted X-ray data at low energy and transmitted X-ray data at high energy, and using the data stored in the storage section 94 for comparison, a foreign substance inspection and the like in inspecting regions at different thickness-direction positions can be performed. Alternatively, as shown in FIG. 18, by preparing, in an image processor 70b, a storage section 96 for holding both transmitted X-ray data at low energy and transmitted X-ray data at high energy, and using the data stored in the storage section 96 for comparison, a foreign substance inspection and the like in inspecting regions at different thickness-direction positions can be performed.

Moreover, in the above-mentioned embodiment, there is provided a configuration including the low-energy detector 32 at an upstream side in the conveying direction A, and at a downstream side, a high-energy detector 42, however, the high-energy detector 42 may be provided at an upstream side in the conveying direction A, and the low-energy detector 32, at a downstream side. Further, in the above-mentioned embodiment, the detection timing of the high-energy detector 42 is delayed by a predetermined time T, however, as long as the inspecting region E is included in the region R1 and the region R2, the detection timing of the low-energy detector 32 may be advanced by a predetermined time T conversely, or it may be possible to advance the detection timing of the low-energy detector 32 as well as delay the detection timing of the high-energy detector 42 so as to shift both detection timings by a predetermined time T. Moreover, in the above-mentioned embodiment, the detection timing in the two ranges of low energy and high energy is controlled, however, it may of course be possible to control the detection timing in three or more ranges.

What is claimed is:

1. A radiation detection device that detects radiation irradiated from a radiation source to a subject having a predetermined thickness and transmitted through the subject, comprising:
   a first detector that detects radiation having been transmitted through a first region extending in a thickness direction within the subject;
   a second detector that detects radiation having been transmitted through a second region extending in a thickness direction within the subject; and
   a timing control section that controls detection timing of radiation in the first detector and the second detector so that an inspecting region located at a predetermined site within the subject is included in the first region and the second region,
   wherein the timing control section controls the detection timing by changing a delay time delaying the detection timing of the second detector relative to the detection timing of the first detector, and
   wherein the delay time is calculated based on a magnification ratio being a ratio of a distance between the radiation source and an inspection center of the subject to a distance between the radiation source and the first detector or the second detector.

2. The radiation detection device according to claim 1, wherein the second detector is arranged in parallel to the first detector with a dead zone region having a predetermined width sandwiched therebetween.

3. The radiation detection device according to claim 2, wherein the width of the dead zone region is a width along a short-side direction of the first detector or the second detector and smaller than a sensing width to sense radiation in the first detector or the second detector.

4. The radiation detection device according to claim 2, wherein the delay time is calculated based on further the width of the dead zone region and a conveying speed at which the subject passes through the dead zone region.

5. The radiation detection device according to claim 1, wherein the timing control section controls the detection timing by outputting a control pulse signal to the second detector, the control pulse signal to the second detector being the same frequency as that of a control pulse signal to the first detector and being delayed in a rising spot of a pulse by the delay time.

6. A radiation image acquiring system comprising:
   the radiation detection device according to claim 1; and
   a timing calculating section that calculates the detection timing of radiation in the first detector and the second detector.

7. The radiation image acquiring system according to claim 6,
   wherein the timing calculating section calculates the detection timing based on a thickness-direction position of a predetermined site within the subject where the inspecting region is located.

8. The radiation image acquiring system according to claim 6,
   wherein the timing calculating section, in the first region, calculates a first reference plane intersecting with a thickness direction of the subject based on a thickness-direction position where the inspecting region is located and, in the second region, calculates a second reference plane being at the same thickness-direction position as that of the first reference plane and intersecting with the thickness direction, and calculates the detection timing so that the first reference plane and the second reference plane are overlapped with each other.

9. The radiation image acquiring system according to claim 6,
   wherein the first detector and the second detector detect radiation having been transmitted through an adjusting subject having a test piece placed at a site thereof corresponding to the inspecting region, and
   wherein the timing calculating section, based on radiation data having been transmitted through the adjusting subject detected by the first detector and the second detector, calculates detection timing of the radiation in the first detector and the second detector so that the test piece is included in the first region and the second region.

10. The radiation image acquiring system according to claim 6, further comprising a composite image generating section that generates a composite image by synthesizing radiation data detected by the first detector with radiation data detected by the second detector, wherein the composite image generating section generates a composite image targeting a plurality of inspecting regions different in thickness-direction position from one set of radiation data detected by the first detector in one first region and a plurality of sets of radiation data detected by the second detector in a plurality of second regions.

11. A radiation image acquiring system comprising:
a radiation detection device that detects radiation irradiated from a radiation source to a subject having a predetermined thickness and transmitted through the subject, the radiation detection device including:
   a first detector that detects radiation having been transmitted through a first region extending in a thickness direction within the subject;
   a second detector that detects radiation having been transmitted through a second region extending in a thickness direction within the subject; and
   a timing control section that controls detection timing of radiation in the first detector and the second detector so that an inspecting region located at a predetermined site within the subject is included in the first region and the second region; and
a timing calculating section that calculates the detection timing of radiation in the first detector and the second detector,
wherein the timing calculating section, in the first region, calculates a first reference plane intersecting with a thickness direction of the subject based on a thickness-direction position where the inspecting region is located and, in the second region, calculates a second reference plane being at the same thickness-direction position as that of the first reference plane and intersecting with the thickness direction, and calculates the detection timing so that the first reference plane and the second reference plane are overlapped with each other.

12. A method of detecting radiation in a radiation detection device including a radiation source, a first detector, a second detector and a timing control section, the method comprising:
   irradiating radiation to a subject having a predetermined thickness from the radiation source;
   detecting radiation irradiated in the irradiating and transmitted through a first region extending in a thickness direction within the subject by the first detector;
   detecting radiation irradiated in the irradiating and transmitted through a second region extending in a thickness direction within the subject by the second detector; and
   controlling, by the timing control section, detection timing of radiation in the first detector and the second detector so that an inspecting region located at a predetermined site within the subject is included in the first region and the second region,
   wherein, in the controlling, the timing control section controls the detection timing by changing a delay time delaying the detection timing of the second detector relative to the detection timing of the first detector, and
   wherein the delay time is calculated based on a magnification ratio being a ratio of a distance between the radiation source and an inspection center of the subject to a distance between the radiation source and the first detector or the second detector.

13. The method of detecting radiation according to claim 12,
   wherein the second detector is arranged in parallel to the first detector with a dead zone region having a predetermined width sandwiched therebetween, and
   wherein the delay time is calculated based on further the width of the dead zone region and a conveying speed at which the subject passes through the dead zone region.

14. The method of detecting radiation according to claim 12,
   wherein, in the controlling, the timing control section controls the detection timing by outputting a control pulse signal to the second detector, the control pulse signal to the second detector being the same frequency as that of a control pulse signal to the first detector and being delayed in a rising spot of a pulse by the delay time.

15. A method of detecting radiation in a radiation image acquiring system including a radiation source, a first detector, a second detector, a timing control section and a timing calculating section, the method comprising:
   irradiating radiation to a subject having a predetermined thickness from the radiation source;
   detecting radiation irradiated in the irradiating and transmitted through a first region extending in a thickness direction within the subject by the first detector;
   detecting radiation irradiated in the irradiating and transmitted through a second region extending in a thickness direction within the subject by the second detector; and
   calculating, in the first region, a first reference plane intersecting with a thickness direction of the subject based on a thickness-direction position where an inspecting region is located and calculating, in the second region, a second reference plane being at the same thickness-direction position as that of the first reference plane and intersecting with the thickness direction, and calculating the detection timing so that the first reference plane and the second reference plane are overlapped with each other, by the timing calculating section; and
   controlling, by the timing control section, detection timing of radiation in the first detector and the second detector so that an inspecting region located at a predetermined site within the subject is included in the first region and the second region.

* * * * *